US00PP07911P

United States Patent [19]

van Andel

[11] Patent Number: Plant 7,911

[45] Date of Patent: Jul. 14, 1992

[54] CARNATION NAMED STASUNDEL

[75] Inventor: Jacob van Andel, Aalsmeer, Netherlands

[73] Assignee: Van Staaveren B.V., Aalsmeer, Netherlands

[21] Appl. No.: 611,510

[22] Filed: Nov. 13, 1990

[51] Int. Cl.[5] ..... A01H 5/00

[52] U.S. Cl. ..... Plt./70.4

[58] Field of Search ..... Plt./70

*Primary Examiner*—Howard J. Locker

*Attorney, Agent, or Firm*—Charles W. Rummler

[57] ABSTRACT

A new and original mini-spray carnation variety particularly distinguished by its Dresden yellow-colored blossoms, which bloom continuously during the Spring, Summer, and Fall blooming periods. The plant itself has a vigorous and spreading growth habit and a height of about 100 cm.

1 Drawing Sheet

BACKGROUND OF THE NEW PLANT

This new mini-spray carnation cultivar originated as a hybrid seedling developed by me in 1985 at our nursery in Aalsmeer, Holland by crossing two varieties selected from our collection of carnations maintained for breeding purposes at Aalsmeer. This particular seedling was selected for propagation because of its spreading growth habit and the yellow coloration of its blossoms. Asexual propagation of this selected plant was done by means of cuttings under my direction at Aalsmeer. Propagation of this new plant by cuttings was continued through successive generations to determine whether the novel characteristics of the selected seedling would be retained from generation to generation and its homogeneity could be assured.

This proved to be successful and this new mini-spray carnation variety is now being propagated at Aalsmeer.

DESCRIPTION OF THE DRAWING

My new mini-spray carnation cultivar is illustrated by the accompanying full-color photographic drawing, which shows blooming portions of spray stems with buds and flowers in several stages of development. The color rendition is as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to The R.H.S. Colour Chart published by The Royal Horticultural Society of London, England.

THE PLANT

Origin: Seedling.

Parentage:

*Seed parent.*—Plant No. 84123-3C (unpatented).

*Pollen parent.*—Adelfie (unpatented).

Classification:

*Botanic.*—*Dianthus caryophyllus.*

*Commercial.*—Spray carnation.

Form: Vigorous, spreading bush with hardly any shoots in the flower stem.

Height: In average, about 100 cm.

Main stem:

*Length.*—In average, about 50 cm.

*Growth.*—Vigorous, strong and spreading.

Foliage:

*Number of Leaves.*—Varies with the amount of daylight.

*Leaf size.*—About 100 mm long and 10 mm wide at the fifth node.

*Leaf shape.*—Pointed and curled. Margins: Entire. Texture: Leathery. Color: Upper and under side: Gray-green.

THE BUD

Size: Medium.

*Diameter.*—Averaging about 12 mm.

*Length.*—Averaging about 25 mm.

Shape: Columnar.

Calyx:

*Shape.*—Columnar.

*Size.*—Averaging 15 mm in width and 28 mm in length.

*Splitting.*—The calyx does not split.

*Aspect.*—Smooth.

Flower steam:

*Character.*—Erect.

*Color.*—Gray-green.

*Length.*—Averaging about 50 cm.

THE FLOWER

Blooming habit: Continuous.

Size of flower: Medium.

*Diameter.*—Averaging about 55 mm.

*Depth.*—Averaging about 20 mm.

Borne: Raceme, on single stem.

Shape when first opening: Generally flat.

When mature.—Becomes somewhat rounded.

Petalage:

*Number of petals.*—Many.

*Texture.*—Soft.

*Appearance.*—Velvety.

*Color.*—Both outer and inside petals: Body: 5 C. Base: 5 C. Reverse Side: 5 C.

Flower Stem:

*Length.*—Averaging about 50 cm.

*Character.*—Strong and upright.

Discoloration:

*After full bloom.*—No discoloration.

Persistence: The flowers hang on and dry.
Disease resistance: Resistant to *Fusarium Oxysporum.*
Lasting quality: Averaging about 10 days as a cut flower and 20 days on the plant.

REPRODUCTIVE ORGANS

Stamens:
- Number.—Very few.
- *Arrangement.*—Petaloid.
- *Anthers.*—Size: Small. Color: White-beige.
- Filaments.—Length: 35 mm. Color: White.
- Pollen.—Color: Yellow.

Pistils:
- *Number.*—1.
- *Styles.*—Length: About 45 mm. Color: White.

- *Stigmas.*—Color: Yellow-White.

FRUIT

Fertility: The fruit is fertile.
Shape: Conical.
Color at maturity: Light brown.

I claim:

1. The new and distinctive spray carnation plant, substantially as herein shown and described, particularly characterized by its Dresden yellow flowers, which are produced profusely in racemes on the flowering stem of an upright bush which blooms continuously on a strong, vigorously-spreading bush of medium height.

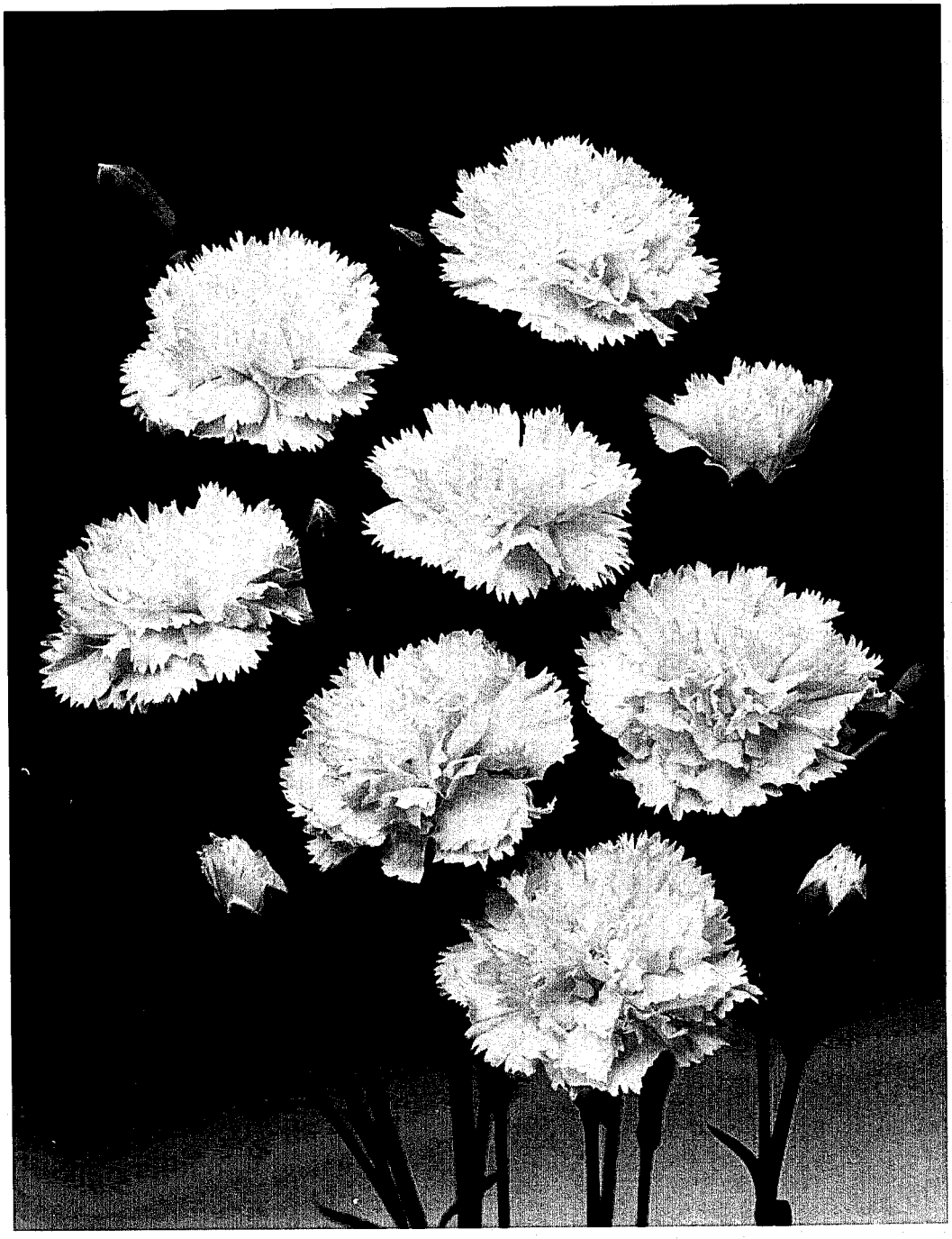

* * * * *